US012171568B2

(12) United States Patent
Hendler et al.

(10) Patent No.: US 12,171,568 B2
(45) Date of Patent: Dec. 24, 2024

(54) NEUROFEEDBACK AND INDUCTION OF AN IMMUNE RESPONSE

(71) Applicants: TECHNION RESEARCH & DEVELOPMENT FOUNDATION LIMITED, Haifa (IL); ICHILOV TECH LTD., Tel Aviv (IL); RAMOT AT TEL-AVIV UNIVERSITY LTD., Tel Aviv (IL)

(72) Inventors: Talma Hendler, Tel Aviv (IL); Asya Rolls, Haifa (IL); Nitzan Lubianiker, Haifa (IL); Tamar Koren, Haifa (IL); Neomi Singer, Givatayim (IL); Tamar Ben Shannan, Haifa (IL); Shai Shen Orr, Karkur (IL); Fahed Hakim, Nazareth (IL); Hilla Azulay-Debby, Nazareth (IL); Rani Cohen, Haifa (IL)

(73) Assignees: TECHNION RESEARCH & DEVELOPMENT FOUNDATION LIMITED, Haifa (IL); ICHILOV TECH LTD., Tel Aviv (IL); RAMOT AT TEL-AVIV UNIVERSITY LTD., Tel Aviv (IL)

( * ) Notice: Subject to any disclaimer, the term of this patent is extended or adjusted under 35 U.S.C. 154(b) by 483 days.

(21) Appl. No.: 17/435,906

(22) PCT Filed: Mar. 3, 2020

(86) PCT No.: PCT/IL2020/050240
§ 371 (c)(1),
(2) Date: Sep. 2, 2021

(87) PCT Pub. No.: WO2020/178820
PCT Pub. Date: Sep. 10, 2020

(65) Prior Publication Data
US 2022/0151542 A1    May 19, 2022

Related U.S. Application Data

(60) Provisional application No. 62/813,059, filed on Mar. 3, 2019.

(51) Int. Cl.
*A61B 5/00* (2006.01)
*A61B 5/055* (2006.01)
(Continued)

(52) U.S. Cl.
CPC .............. *A61B 5/411* (2013.01); *A61B 5/055* (2013.01); *A61B 5/378* (2021.01); *A61B 5/4833* (2013.01); *A61B 5/486* (2013.01); *A61B 10/0035* (2013.01)

(58) Field of Classification Search
None
See application file for complete search history.

(56) References Cited

PUBLICATIONS

Luctkar-Flude, M., Groll, D., & Tyerman, J. (2017). Using neurofeedback to manage long-term symptoms in cancer survivors: Results of a survey of Neurofeedback Providers. European Journal of Integrative Medicine, 12, 172-176 (Year: 2017).*

(Continued)

*Primary Examiner* — John R Downey
*Assistant Examiner* — Anant A Gupta
(74) *Attorney, Agent, or Firm* — The Roy Gross Law Firm, LLC; Roy Gross

(57) ABSTRACT

The present invention is directed to a method for inducing an immune response in a subject, including a step of activating neurons in the mesolimbic network of the subject by applying a neurofeedback.

13 Claims, 12 Drawing Sheets

(51) Int. Cl.
A61B 5/378 (2021.01)
A61B 10/00 (2006.01)

(56) References Cited

PUBLICATIONS

Sulzer, J., Sitaram, R., Blefari, M. L., Kollias, S., Birbaumer, N., Stephan, K. E., Luft, A., & Gassert, R. (2013). Neurofeedback-mediated self-regulation of the dopaminergic midbrain. NeuroImage, 83, 817-825 (Year: 2013).*

Schummer, G. J., Noh, S. M., & Mendoza, J. J. (2013). The effect of neurofeedback and cranial electrotherapy on immune function within a group of HIV+ subjects: A controlled study. Journal of Neurotherapy, 17(3), 151-161 (Year: 2013).*

Ben-Shaanan TL, Schiller M, Azulay-Debby H, Korin B, Boshnak N, Koren T, Krot M, Shakya J, Rahat MA, Hakim F, Rolls A. Modulation of anti-tumor immunity by the brain's reward system. Nat Commun. Jul. 13, 2018;9(1):2723. doi: 10.1038/s41467-018-05283-5. PMID: 30006573; PMCID: PMC6045610.

Hendler, T. & Lubianiker, N., Tel-Aviv Sourasky Medical Center, (Jan. 20, 2019—estimated Jun. 30, 2022). Characterization of the Relationship Between the Human Mesolimbic Reward System and Immune Functioning. Identifier NCT03951870. https://clinicaltrials.gov/ct2/show/NCT03951870.

MacInnes JJ, Dickerson KC, Chen NK, Adcock RA. Cognitive Neurostimulation: Learning to Volitionally Sustain Ventral Tegmental Area Activation. Neuron. Mar. 16, 2016;89(6):1331-1342. doi: 10.1016/j.neuron.2016.02.002. Epub Mar. 3, 2016. PMID: 26948894; PMCID: PMC5074682.

Schummer, G. J., Noh, S. M., & Mendoza, J. J. (2013). The effect of neurofeedback and cranial electrotherapy on immune function within a group of HIV+ subjects: A controlled study. Journal of Neurotherapy, 17(3), 151-161. https://doi.org/10.1080/10874208.2013.813168.

Koush Y, Ashburner J, Prilepin E, Sladky R, Zeidman P, Bibikov S, Scharnowski F, Nikonorov A, De Ville DV. OpenNFT: An open-source Python/Matlab framework for real-time fMRI neurofeedback training based on activity, connectivity and multivariate pattern analysis. Neuroimage. Aug. 1, 2017;156:489-503. doi: 10.1016/j.neuroimage.2017.06.039. Epub Jun. 21, 2017. PMID: 28645842.

Goebel MU, Trebst AE, Steiner J, Xie YF, Exton MS, Frede S, Canbay AE, Michel MC, Heemann U, Schedlowski M. Behavioral conditioning of immunosuppression is possible in humans. Faseb J. Dec. 2002;16(14):1869-73. doi: 10.1096/fj.02-0389com. PMID: 12468450.

Albring A, Wendt L, Benson S, Witzke O, Kribben A, Engler H, Schedlowski M. Placebo effects on the immune response in humans: the role of learning and expectation. PLoS One. 2012;7(11):e49477. doi: 10.1371/journal.pone.0049477. Epub Nov. 21, 2012. PMID: 23185342; PMCID: PMC3504052.

Sternberg EM. Neural regulation of innate immunity: a coordinated nonspecific host response to pathogens. Nat Rev Immunol. Apr. 2006;6(4):318-28. doi: 10.1038/nri1810. PMID: 16557263; PMCID: PMC1783839.

Pavlov VA, Tracey KJ. Neural regulation of immunity: molecular mechanisms and clinical translation. Nat Neurosci. Feb. 2017;20(2):156-166. doi: 10.1038/nn.4477. Epub Jan. 16, 2017. PMID: 28092663.

Dunn JH, Ellis LZ, Fujita M. Inflammasomes as molecular mediators of inflammation and cancer: potential role in melanoma. Cancer Lett. Jan. 1, 2012;314(1):24-33. doi: 10.1016/j.canlet.2011.10.001. Epub Oct. 12, 2011. PMID: 22050907.

Iwata M, Ota KT, Duman RS. The inflammasome: pathways linking psychological stress, depression, and systemic illnesses. Brain Behav Immun. Jul. 2013;31:105-14. doi: 10.1016/j.bbi.2012.12.008. Epub Dec. 20, 2012. PMID: 23261775; PMCID: PMC4426992.

Besedovsky HO, del Rey A. Central and peripheral cytokines mediate immune-brain connectivity. Neurochem Res. Jan. 2011;36(1):1-6. doi: 10.1007/s11064-010-0252-x. Epub Sep. 4, 2010. PMID: 20820913.

Dantzer R, O'Connor JC, Freund GG, Johnson RW, Kelley KW. From inflammation to sickness and depression: when the immune system subjugates the brain. Nat Rev Neurosci. Jan. 2008;9(1):46-56. doi: 10.1038/nrn2297. PMID: 18073775; PMCID: PMC2919277.

Sitaram, R., Ros, T., Stoeckel, L. et al. Closed-loop brain training: the science of neurofeedback. Nat Rev Neurosci 18, 86-100 (2017). https://doi.org/10.1038/nrn.2016.164.

Paret C, Ruf M, Gerchen MF, Kluetsch R, Demirakca T, Jungkunz M, Bertsch K, Schmahl C, Ende G. fMRI neurofeedback of amygdala response to aversive stimuli enhances prefrontal-limbic brain connectivity. Neuroimage. Jan. 15, 2016;125:182-188. doi: 10.1016/j.neuroimage.2015.10.027. Epub Oct. 16, 2015. PMID: 26481674.

Sulzer J, Sitaram R, Blefari ML, Kollias S, Birbaumer N, Stephan KE, Luft A, Gassert R. Neurofeedback-mediated self-regulation of the dopaminergic midbrain. Neuroimage. Dec. 2013;83:817-25. doi: 10.1016/j.neuroimage.2013.05.115. Epub Jun. 19, 2013. PMID: 23791838.

Esteban O, Markiewicz CJ, Blair RW, Moodie CA, Isik AI, Erramuzpe A, Kent JD, Goncalves M, DuPre E, Snyder M, Oya H, Ghosh SS, Wright J, Durnez J, Poldrack RA, Gorgolewski KJ. fMRIPrep: a robust preprocessing pipeline for functional MRI. Nat Methods. Jan. 2019;16(1):111-116. doi: 10.1038/s41592-018-0235-4. Epub Dec. 10, 2018. PMID: 30532080; PMCID: PMC6319393.

Oe, M., Kobayashi, Y., Ishida, T., Chiba, H., Matsuoka, M., Kakuma, T., Frewen, P. and Olff, M., 2020. Screening for psychotrauma related symptoms: Japanese translation and pilot testing of the Global Psychotrauma Screen. European journal of psychotraumatology, 11(1), p. 1810893.

Sakakibara, M., Sato, Y., Sakeuchi, S., Suin, P., Ou, O., 2019. Clinical Applications of Biofeedback/Neurofeedback. Psychosm. Med., 2019, vol. 59, pp. 613-621.

* cited by examiner

NEUROFEEDBACK AND INDUCTION OF AN IMMUNE RESPONSE

CROSS-REFERENCE TO RELATED APPLICATIONS

This application is a National Phase of PCT Patent Application No. PCT/IL2020/050240 having International filing date of Mar. 3, 2020, which claims the benefit of priority of U.S. Provisional Patent Application No. 62/813,059 titled "NEUROFEEDBACK AND INDUCTION OF AN IMMUNE RESPONSE", filed Mar. 3, 2019, the contents of which are incorporated herein by reference in their entirety.

FIELD OF INVENTION

The present invention, in some embodiments thereof, is in the field of neuroimmunology and neuromodulation.

BACKGROUND

The placebo response, which is associated with the neuronal reward system, is one of the most fascinating phenomenon in modern medicine, and an example for the potency of the mental state to affect one's clinical state and general well-being. Deciphering the neuronal mechanism mediating brain-body interactions, as manifested in the placebo response, harbors a potential to utilize the curative capacities of the brain. Recently, a causal link between activation of the reward system and an immune function was reported in mice. This discovery holds great potential for improving personal health management, rationalizing the use of reward-related brain activation to enhance immune function.

Biofeedback, a technique developed in the 1960s, teaches individuals how to regulate autonomic bodily functions normally considered to be outside of the realm of conscious control. Biofeedback is founded on the concept that immediate and continuous feedback of information will amplify a conditioned response so that voluntary control can be achieved. Biofeedback can train people to consciously regulate autonomic functions such as heart rate, skin conductance, and bowel and bladder function, and has even allowed individuals to modulate higher-level unconscious biological processes such as pain, athletic performance, and anxiety. The training of brain activity or connectivity, i.e., brain functionality, by means of biofeedback, is termed neurofeedback (NF). Generally, neurofeedback relates to a brain-computer interphase approach, i.e., closing a loop with the brain via a computerized interface. Learning by neurofeedback can include both volitional and non-volitional techniques.

SUMMARY

According to a first aspect, there is provided a method for inducing an immune response in a subject, comprising the step of activating a mesolimbic neuron in the subject by applying a neurofeedback, thereby inducing the immune response in the subject.

In some embodiments, the mesolimbic neuron is located in the ventral tegmental area (VTA), the bilateral ventral striatum (VS), or a combination thereof.

In some embodiments, inducing the immune response comprises activating or increasing the immune response.

In some embodiments, the immune response is selected from the group consisting of: vaccination response, humoral response, cytotoxic response, innate immune response, and acquired immune response.

In some embodiments, the increased vaccination efficacy is determined based on an antibody concentration in the plasma, an antibody biological half-life in the plasma, or a combination thereof, compared to control.

In some embodiments, the neurofeedback comprises electroencephalography (EEG), functional magnetic resonance imaging (fMRI), or a combination thereof.

In some embodiments, the subject is afflicted with an immunodeficient disease.

In some embodiments, the subject is afflicted with an infectious disease.

In some embodiments, the infectious disease is a viral disease.

In some embodiments, the subject is afflicted with cancer.

In some embodiments, the subject is in need of vaccination.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION

Figure 1A:
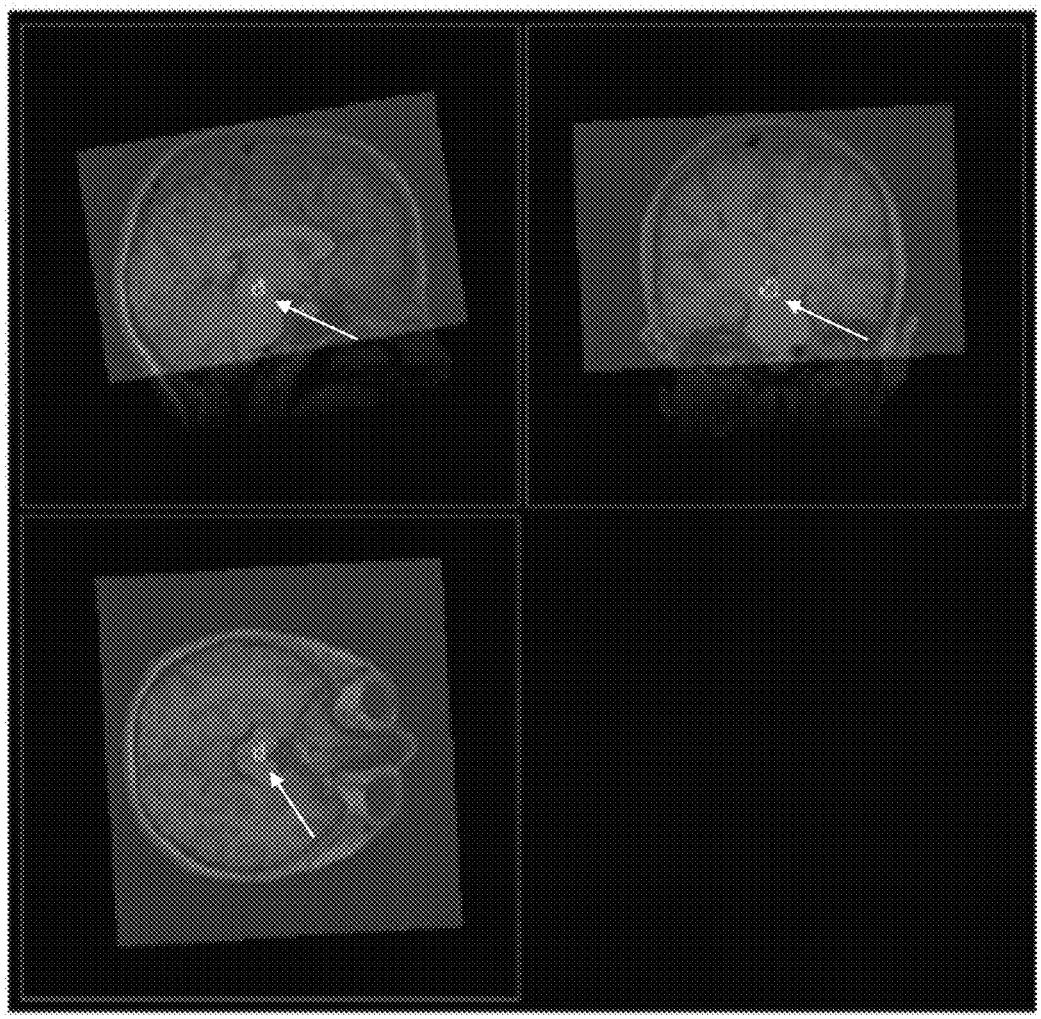
FIGS. 1A-1D are images and graphs of an open neurofeedback training (NFT) online neurofeedback session to (1A, arrows) the ventral tegmental area (VTA), showing the individually selected region for regulation based on a functional localizer task and on an anatomical restriction mask based on the literature. The three time courses represent the head movements (1B), the raw blood oxygenation level dependent (BOLD) levels from the VTA (1C), and the calculated data, which is presented to the subject, after controlling for different artifacts (1D).
Figure 1B:
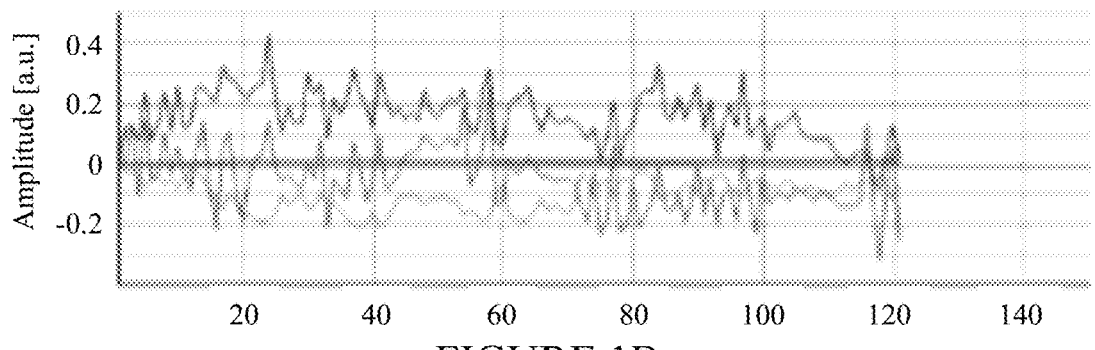
Figure 1C:
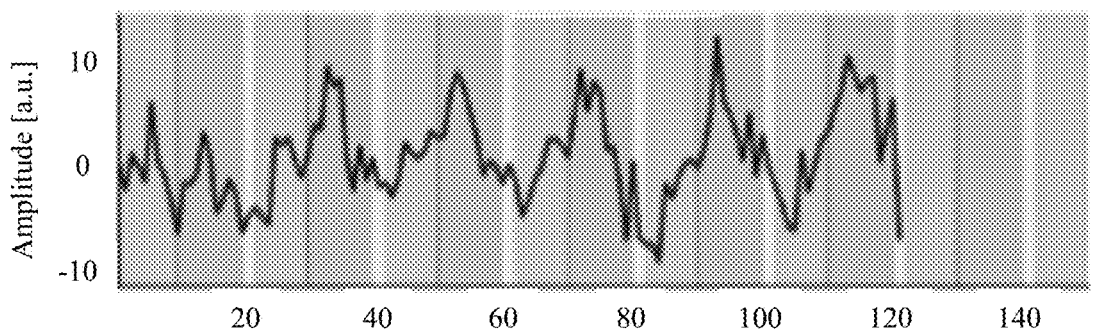
Figure 1D:
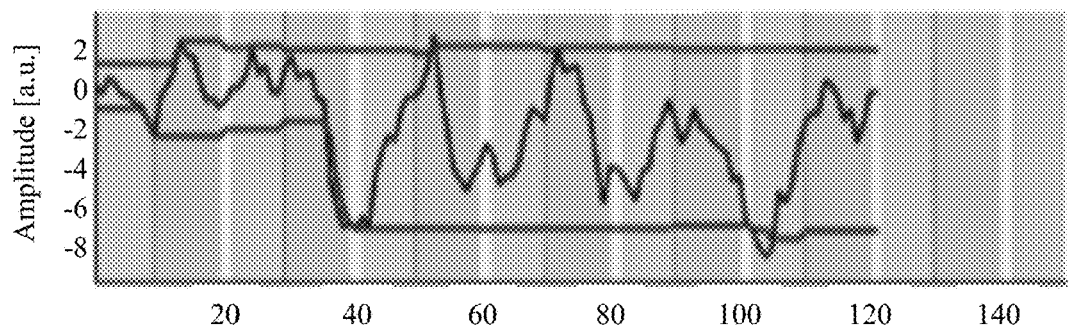
Figure 2:
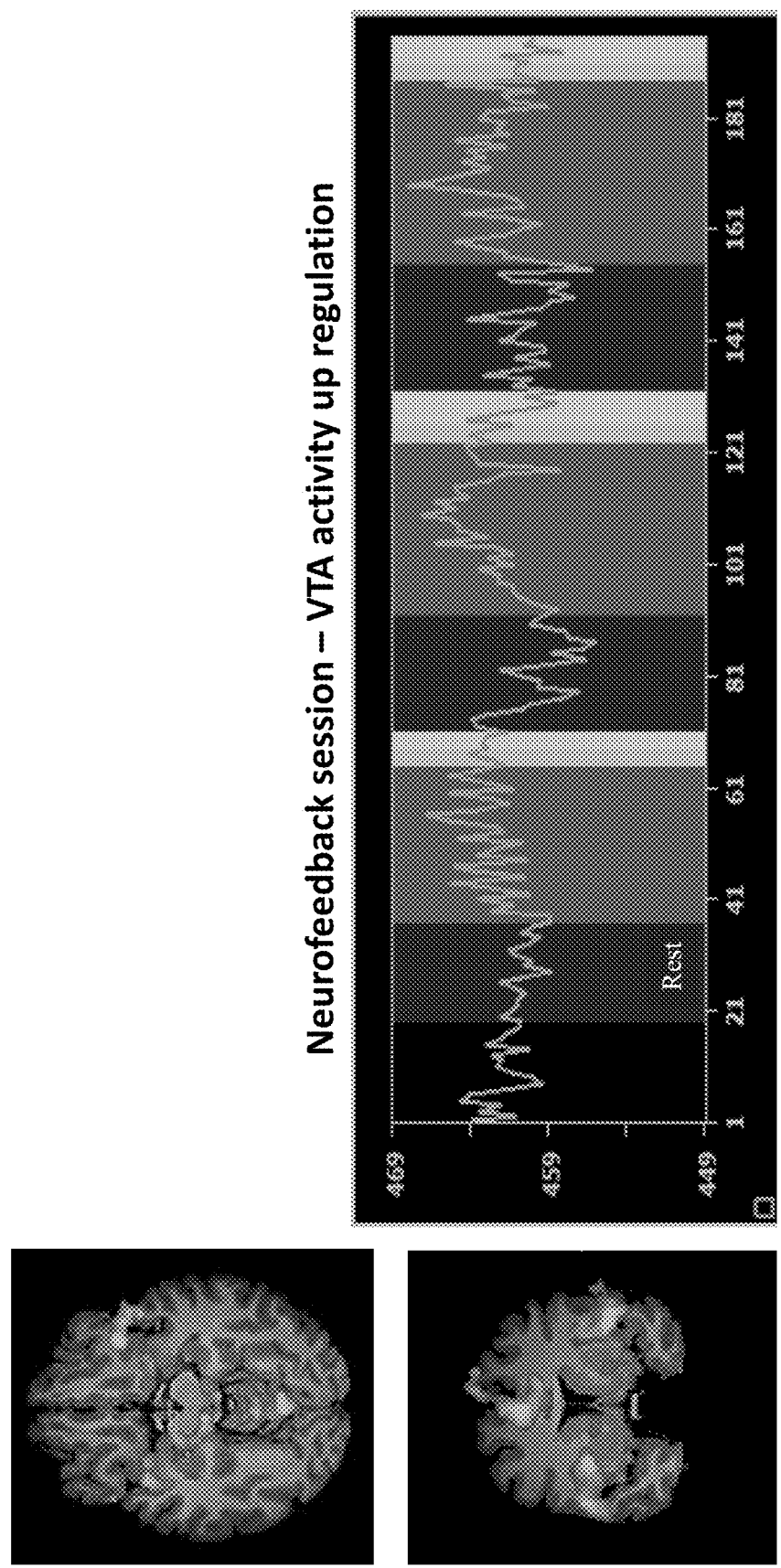
FIG. 2 is images and a graph showing a neurofeedback session offline analysis, which validated the real-time calculation and demonstrated the ability of a subject to up regulate his VTA activity, along with other mesolimbic activations (left, bilateral ventral striatum, and bilateral anterior Insula).
Figure 3A:
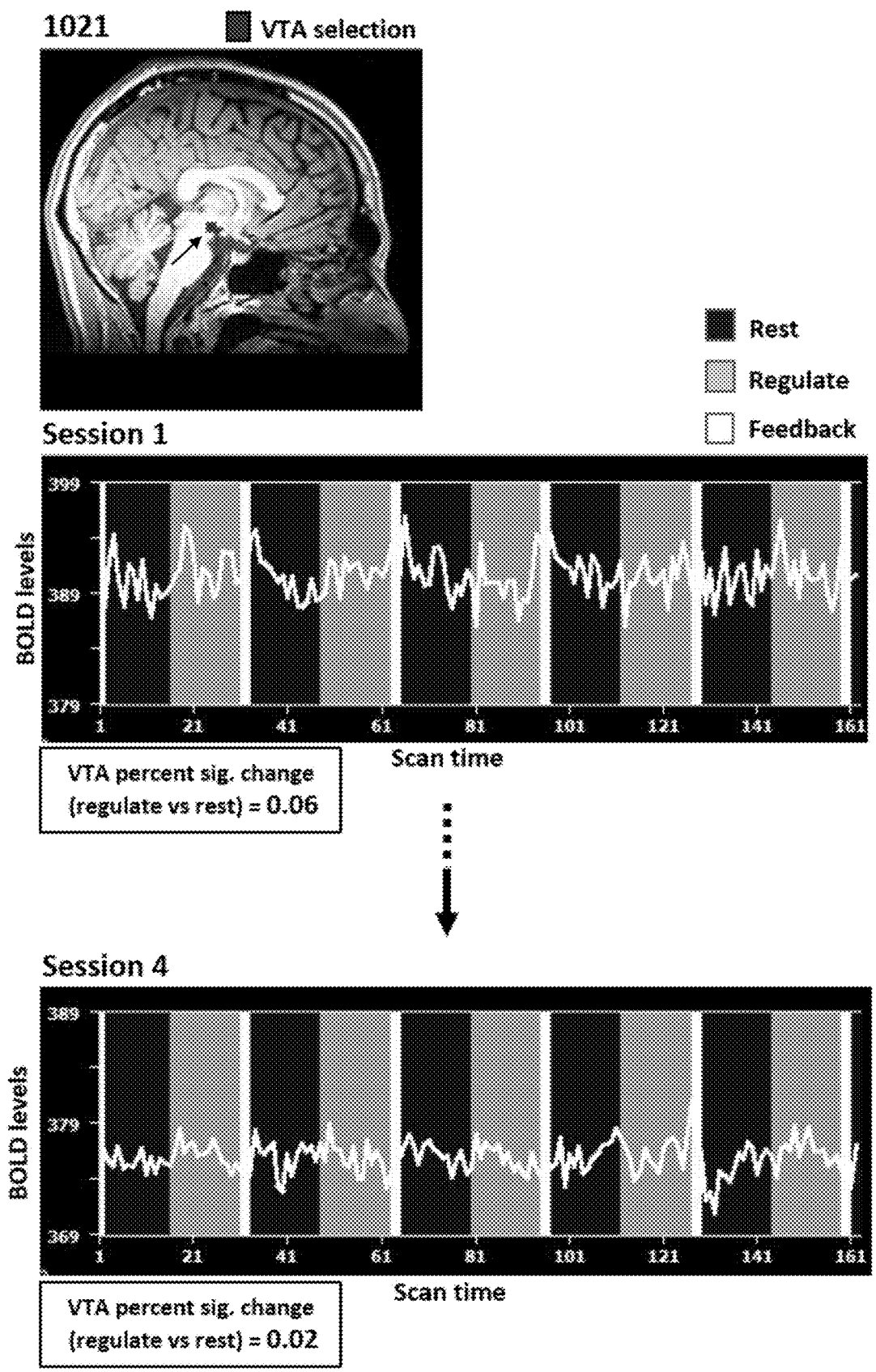
FIGS. 3A-3D are images and graphs of three subjects (two males and one female; mean age—24.3 years old): 1021 (3A), 1022 (3B), and 1023 (3C), that participated in four functional magnetic resonance imaging neurofeedback (fMRI-NF) training sessions. All subjects were to be vaccinated before traveling abroad or as a part of their clinical studies. Individual VTA region of interest was selected based on an anatomical restriction mask and performance in a functional localizer task (monetary incentive delay task, arrows). Each NF training session lasted for approximately 30 minutes, and included three runs of five NF cycles each, comprising of three alternating conditions: "Rest", "Regulate" and "Feedback"; for subjects 1022 (3B) and 1023 (3C) a task "Baseline" condition was added to account for general signal artifacts and to allow better statistical inference. Data were preprocessed (slice scan time correction, 3D motion correction, temporal filtering and spatial smoothing); mean BOLD values in the VTA for each condition were then extracted. The mean VTA percent signal change for the contrast between "Rest" and "Regulate" conditions for each subject is presented separately, and a graph showing scores for all three subjects. (3D) is a vertical bar graph showing comparative results representing the subjects' first and last attempt to apply mental strategies in order to up regulate their VTA BOLD signal.
Figure 3B:
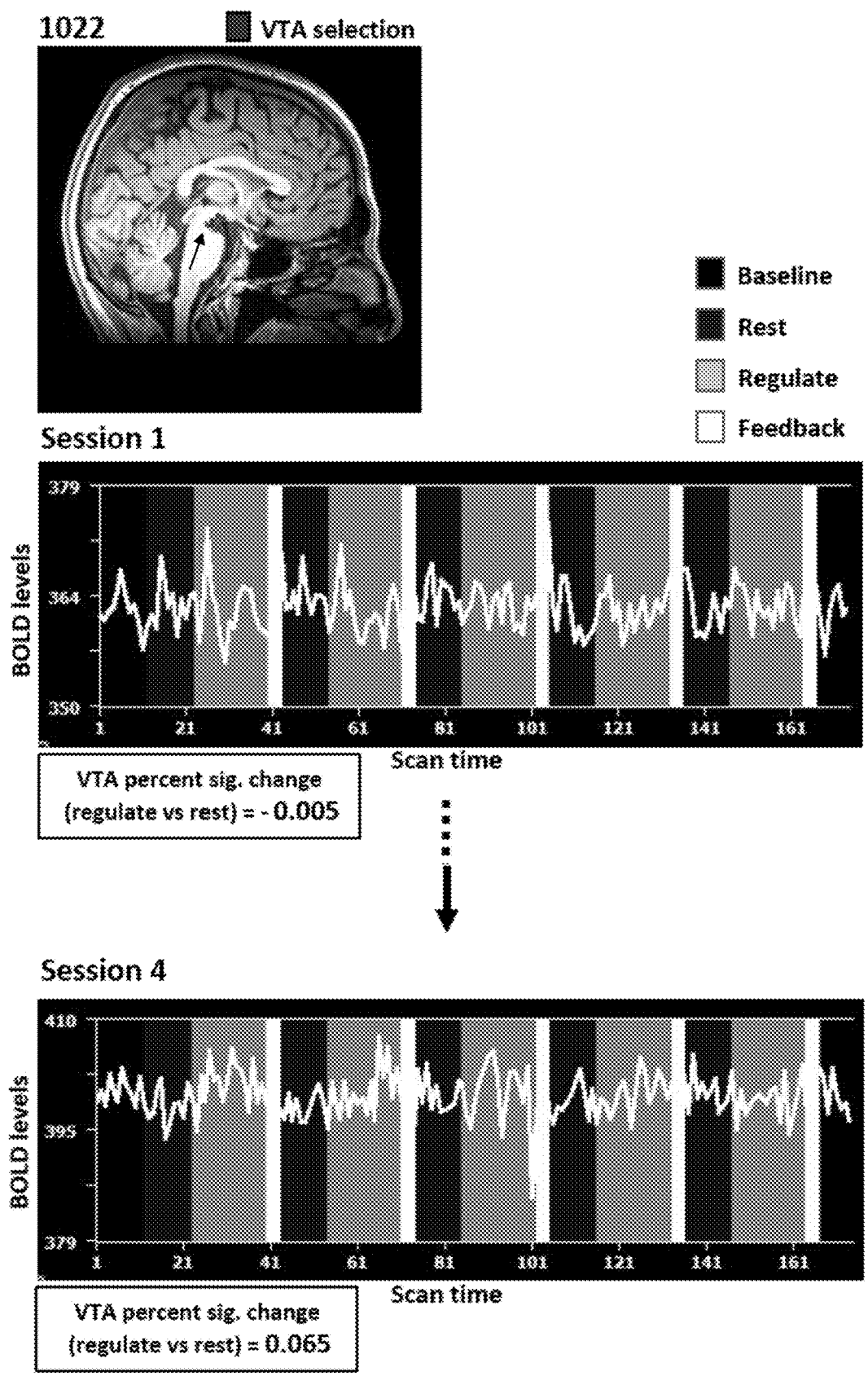
Figure 3C:
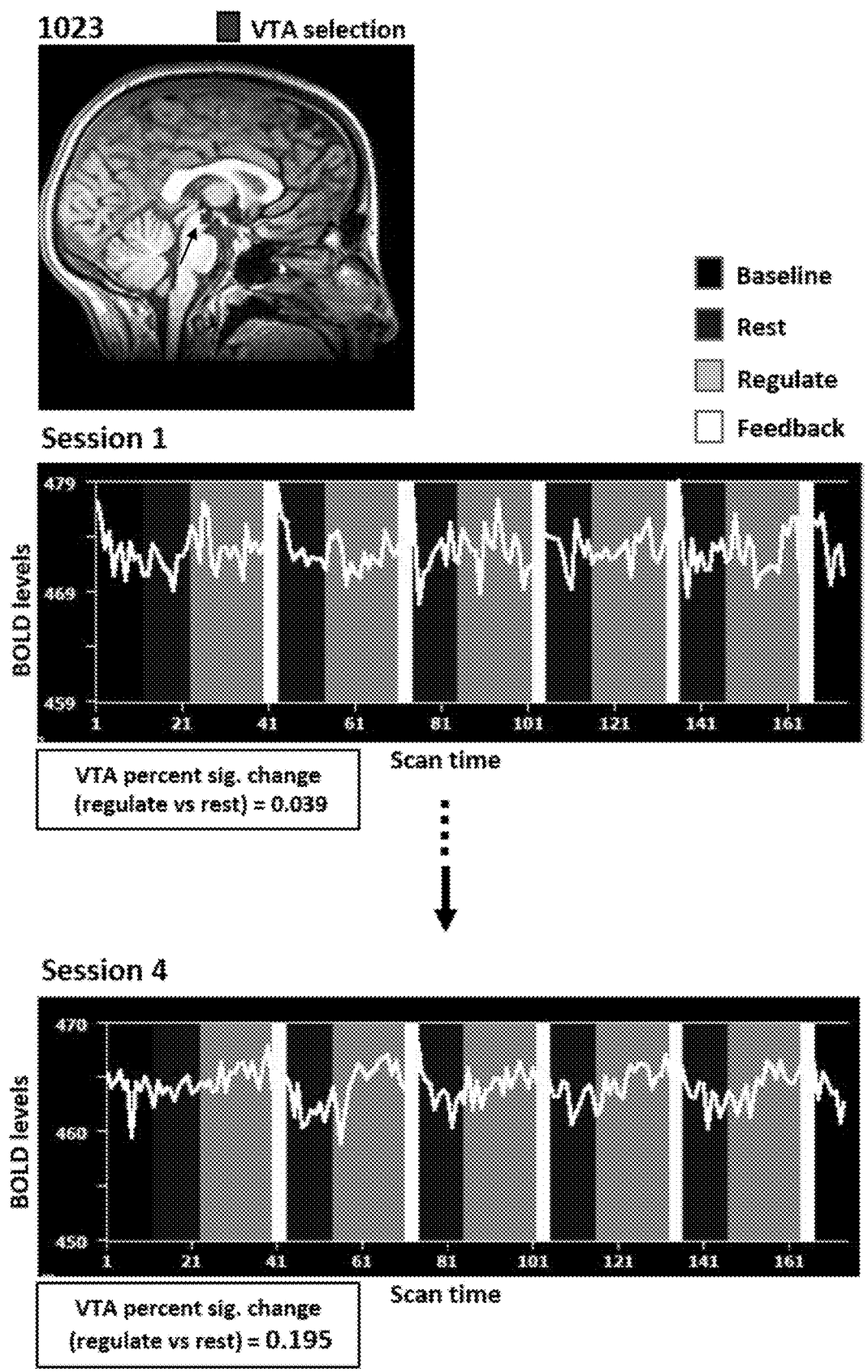
Figure 3D:
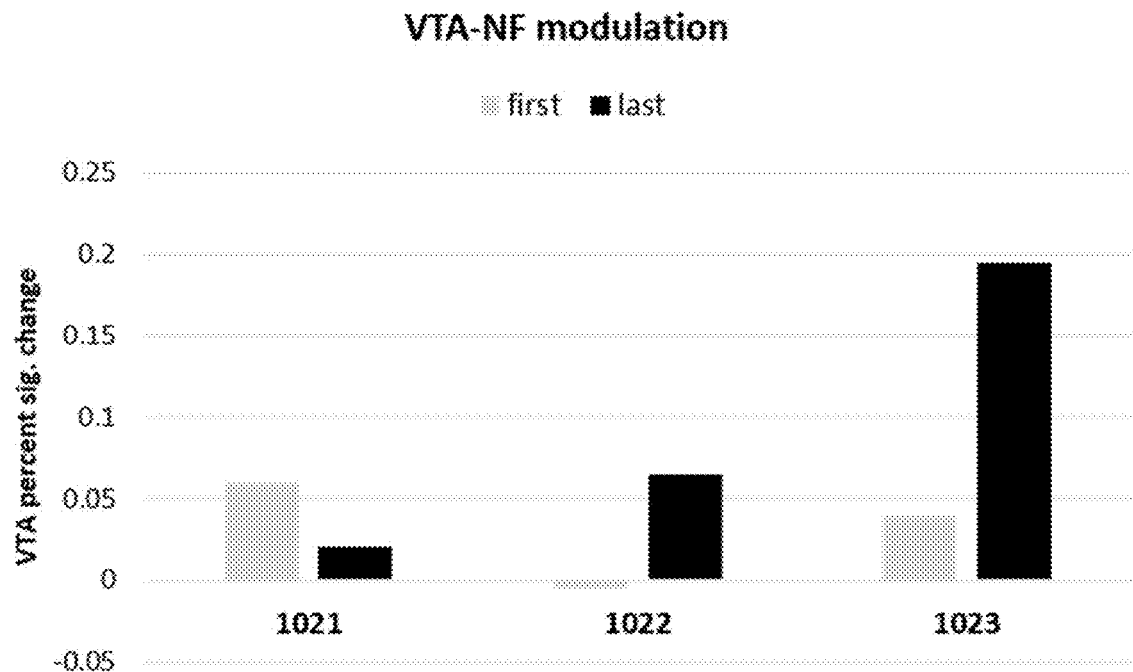

In some embodiments, the present invention is directed to a method for inducing an immune response in a subject, comprising the step of activating a mesolimbic neuron in the subject by applying a neurofeedback (NF), thereby inducing the immune response in the subject.

In some embodiments, a mesolimbic neuron is located in the ventral tegmental area (VTA), in the bilateral ventral striatum (VS), or a combination thereof.

In some embodiments, activating a mesolimbic neuron comprises co-activating a neuron located in the VTA and a neuron located in the VS.

In some embodiments, inducing an immune response is increasing, elevating, activating, or differentially activating an immune response, or any combination thereof.

In some embodiments, an immune response comprises any response taken by the body to defend itself from pathogens or abnormalities. In one embodiment, an immune response comprises a response mediated or involving an immune cell.

In one embodiment, an immune response comprises any response activating or inhibiting the immune system or mediators of the immune system. In another embodiment, activation of an immune response comprises activation of an immune cell. In another embodiment, activation of an immune cell results in the proliferation of a sub-set of immune cells. In another embodiment, activation of an immune cell results in increased secretion of an immunologic mediator by the activated cell. In another embodiment, activation of an immune cell results in the engulfment and/or destruction of a pathogen, a foreign cell, a diseased cell, a molecule derived or secreted therefrom, or any combination thereof. In another embodiment, activation of an immune cell results in the engulfment and or destruction of a neighboring cell, such as, but not limited to, a cell infected by a virus. In another embodiment, activation of an immune cell results in activating the secretion of antibodies directed to a certain molecule, epitope, pathogen, or any combination thereof.

In some embodiments, an immune response is a cytotoxic response. As used herein, cytotoxic response refers to a response comprising activation of the complement system, leading to cell lysis and/or other damage.

In some embodiments, an immune response is a humoral response, i.e., involves production and secretion of antibodies.

In some embodiments, an immune response is an innate response, i.e., involves the innate immune system.

In some embodiments, an immune response is an acquired immune response, i.e., involves the acquired immune response.

In some embodiments, an immune response is any response activating: B-cells, Dendritic cells, macrophages, Natural Killer (NK) cells, T-cells, Thymocytes, or any combination thereof. In another embodiment, a response activating a cell as described herein, results in: proliferation of the cell or another immune cell, secretion of immune mediators, such as cytokines, migration of an immune cell, activation of an immune cascade, elimination of foreign molecules or cells, or any combination thereof.

In another embodiment, an immune response is associated with a disease and a method described herein is used to optimize the immune response according to the exact condition.

In some embodiments, applying the method of the invention results in increased production, secretion, or both, of one or more cytokines. In some embodiments, the one or more cytokines is selected from: TNFα, INFγ, IL-6, IL-4, and/or any combination thereof.

In another embodiment, an immune response is associated with cancer therapy wherein the immune response is triggered against tumor/cancer cells or cancer/tumor antigens. In another embodiment, the method of the invention for inducing an immune response has a direct positive impact on cancer therapy.

In some embodiments, an immune response is a vaccination response. In some embodiments, the method of the present invention is directed to optimizing vaccination. In some embodiments, optimized vaccination results in increased vaccination effectiveness.

The term "effectiveness", such as used herein in conjunction with vaccination, refers to how well (e.g., the level or extent) a compound, a material, a drug, a composition, a vaccine, or any treatment utilizing an equivalent thereof, works in practice (i.e., treating subjects), in clinical trials (e.g., research studies), or both.

The terms "efficacy" and "effectiveness" are used herein interchangeably.

Methods for determining vaccination efficacy or effectiveness are common, and would be apparent to one of ordinary skill in the art.

In some embodiments, increased vaccination efficacy comprises increased concentration, titer, biological half-life, amount, or any combination thereof, of antibodies in the plasma of a subject, compared to control. In some embodiments, increased vaccination efficacy comprises increased production of antibodies in the subject, compared to control. In some embodiments, increased vaccination efficacy comprises increased antibody diversity, compared to control. In some embodiments, increased vaccination efficacy comprises increased antibody arsenal, compared to control. In some embodiments, increased vaccination efficacy comprises an increased antibody repertoire capable of targeting or reacting with a wider range of antigens, compared to control.

As used herein, the term "antibody repertoire" refers to all of the specific types of antibodies which were produced or can be produced by a subject.

In some embodiments, increased vaccination efficacy comprises increased concentration, titer, biological half-life, amount, or any combination thereof, of a specific type of an antibody in the plasma of a subject, compared to control. In some embodiments, increased vaccination efficacy comprises increased production of a specific type of an antibody in the subject, compared to control. As used herein, the specific type of antibody is defined based on: the class to which the antibody belongs (i.e., IgA, IgD, IgE, IgG, and IgM) or a sub-class thereof (e.g., IgA1, IgG1, IgG2, etc.), the specific molecule, or antigen or an epitope thereof, with which the antibody reacts, or any combination thereof.

As used herein, the term "increased production" encompasses increased production yield, increased production rate, increased production capacity, or any combination thereof.

In some embodiments, increased is by at least 5% more, at least 20% more, at least 50% more, at least 75% more, at least 100% more, at least 250% more, at least 500%, at least 750% more, or at least 1,000% more, compared to control, and any value and range therebetween. In some embodiments, increased is by 5-25% more, 20-75% more, 50-120% more, 75-150% more, 100-250% more, 200-550% more, 500-750% more, or 700-1,000% more compared to control. Each possibility represents a separate embodiment of the invention.

In some embodiments, an efficacy-increased vaccine (such as resulting from the performing the method of the invention) induces or promotes production of more antibodies in the subject, compared to control. In some embodiments, an efficacy-increased vaccine results in more antibodies in the plasma of the subject, compared to control. In some embodiments, an efficacy-increased vaccine induces or promotes production of antibodies having increased biological half-life in the plasma compared to control. In some embodiments, an efficacy-increased vaccine results in increased memory response, production or secretion of a specific antibody, antibody repertoire, or any combination thereof.

In one embodiment, the present invention is directed to a method for treating cancer, comprising a step of inducing a mesolimbic neuron. In another embodiment, cancer treatable by the method of the invention comprises solid tumors. In another embodiment, the method of the invention results in growth inhibition of a tumor. In another embodiment, the method of the invention results in inhibiting metastasis.

In another embodiment, cancer treatable by the method described herein is: adrenocortical carcinoma, anal cancer, bladder cancer, brain tumor, brain stem glioma, brain tumor, cerebellar astrocytoma, cerebral astrocytoma, ependymoma, medulloblastoma, supratentorial primitive neuroectodermal, pineal tumors, hypothalamic glioma, breast cancer, carcinoid tumor, carcinoma, cervical cancer, colon cancer, endometrial cancer, esophageal cancer, extrahepatic bile duct cancer, Ewing's family of tumors (PNET), extracranial germ cell tumor, eye cancer, intraocular melanoma, gallbladder cancer, gastric cancer, germ cell tumor, extragonadal, gestational trophoblastic tumor, head and neck cancer, hypopharyngeal cancer, islet cell carcinoma, laryngeal cancer, leukemia, acute lymphoblastic, leukemia, oral cavity cancer, liver cancer, lung cancer, small cell, lymphoma, AIDS-related, lymphoma, central nervous system (primary), lymphoma, cutaneous T-cell, lymphoma, Hodgkin's disease, non-Hodgkin's disease, malignant mesothelioma, melanoma, Merkel cell carcinoma, metastatic squamous carcinoma, multiple myeloma, plasma cell neoplasms, mycosis fungoides, myelodysplastic syndrome, myeloproliferative disorders, nasopharyngeal cancer, neuroblastoma, oropharyngeal cancer, osteosarcoma, ovarian epithelial cancer, ovarian germ cell tumor, ovarian low malignant potential tumor, pancreatic cancer, exocrine, pancreatic cancer, islet cell carcinoma, paranasal sinus and nasal cavity cancer, parathyroid cancer, penile cancer, pheochromocytoma cancer, pituitary cancer, plasma cell neoplasm, prostate cancer, rhabdomyosarcoma, rectal cancer, renal cell cancer, salivary gland cancer, Sezary syndrome, skin cancer, cutaneous T-cell lymphoma, skin cancer, Kaposi's sarcoma, skin cancer, melanoma, small intestine cancer, soft tissue sarcoma, soft tissue sarcoma, testicular cancer, thymoma, malignant, thyroid cancer, urethral cancer, uterine cancer, sarcoma, unusual cancer of childhood, vaginal cancer, vulvar cancer, or Wilms' tumor.

As used herein, the disease is an immune system disorder. In some embodiments, an immune system disorder is associated with abnormally low activity of the immune system. In another embodiment, an immune system disorder is an immune deficiency disease. A non limiting example of an immune deficiency disease is AIDS. In another embodiment, the disease is an inflammatory disease. In another embodiment, the disease is a cell-proliferation-associated disease. In another embodiment, the disease is cancer. In some embodiments, the disease is an infectious disease. In some embodiments, the disease is a viral disease. Types of viral disease would be apparent to one of ordinary skill in the art. In one embodiment, the viral disease is influenza. In one embodiment, the viral disease is Hepatitis B.

As used herein, the term "control" encompasses a subject, or a sample derived therefrom, wherein the subject was not applied with neurofeedback to neurons of the mesolimbic network. In some embodiments, a control subject was not transcranially-stimulated. In some embodiments, a control is a vaccinated subject, or a sample derived therefrom, wherein the control subject was or is not applied with neurofeedback to neurons of the mesolimbic network. In some embodiments, the control is a subject in need of vaccination, or a sample derived therefrom, wherein the control subject was or is not applied with neurofeedback to neurons of the mesolimbic network.

In some embodiments, the control is a response (i.e., an immune response) without or in the absence of neurofeedback application.

According to another embodiment, the method of the invention comprises inducing an immune response in a subject, by co-activating mesolimbic neurons in the VTA and VS in the subject by applying a neurofeedback.

In some embodiments, activating a mesolimbic neuron comprises co-activating a neuron located in the VTA and a neuron located in the VS.

In some embodiments, mesolimbic co-activation (VTA and VS) results in enhanced immune response compared to a single activation (i.e., VTA, or VS). In some embodiments, mesolimbic co-activation (VTA and VS) results in comparable enhancement of immune response compared to a single activation (i.e., VTA, or VS). In some embodiments, mesolimbic co-activation (VTA and VS) results in synergistically enhanced immune response compared to a single activation (i.e., VTA, or VS).

Neurofeedback

In general, the invention is directed to a method of training an individual subject to modify his or her neuronal activity during neurofeedback sessions that utilize real time brain imaging or recording. In some embodiments, the method comprises a step of providing feedback to the subject to enable the subject to modify his or her neuronal activity within the selected brain region, regions, or circuits. In some embodiments, the selected brain target being imaged is associated with a specific disease or disorder.

A subject can be treated using the method, for example, as follows. In some cases, the subject may need to visit a clinic or research facility a plurality of times, depending on the condition of the patient. rt-fMRI neurofeedback is provided to the subject based on images from a specific region or circuit of the brain. In some cases, initial rt-fMRI neurofeedback training runs are used to allow the subject to learn how to use the system, and then actual sessions are completed during which the subject is asked to complete specific cognitive tasks. In subsequent visits, the subject undergoes substantially the same procedures as described with respect to the first visit.

As used herein, "neurofeedback" makes available to a subject a record of one or more of the subject's neurological activities to which the subject ordinarily does not have direct conscious access.

In one embodiment, the method of the present invention is directed to fMRI-based neurofeedback. fMRI measures blood oxygen level dependent (BOLD) T2* weighted signal changes as an indirect way of visualizing neuronal activity in a localized brain area. The terms "fMRI feedback", "fMRI neurofeedback", and the like, are interchangeable, and refer herein to the use of a fMRI device to display or provide a representation of a subject's brain activity to the subject in a real-time or substantially simultaneous manner. As used herein, fMRI is utilized to measure brain activity by detecting changes which are associated with (BOLD) contrast.

In one embodiment, high BOLD value is indicative of highly active neural region. In one embodiment, an active neuron has a greater BOLD level compared to inhibited, repressed, or inactivated neuron. In some embodiments, the use of fMRI neurofeedback may improve the correspondence between first-person experience and specific brain activation patterns in a manner that minimally affects the experience itself. In some embodiments, the use of fMRI provides meditators the ability to enhance their control over their own brain activity. In some embodiments, the use of fMRI neurofeedback directly correlates subjective experience with neural activation. In some embodiments, fMRI neurofeedback data can be integrated and presented to the measured subject via any sort of visual, audio or other sensory mechanism, as would be understood by those skilled in the art. Non-limiting examples include a visual display, an interactive visual display (e.g., video game), an auditory signal, or a tactile signal. Information can further be streamed to the subject, if desired. In some embodiments, the method includes a steps of measuring a subject's mesolimbic network activity by fMRI, presenting a representation of the subject's mesolimbic activity to the subject simultaneously with the measuring, and instructing the subject to alter their meditative state, such that the alteration to their meditative state increases their mesolimbic activity. In some embodiments, the present invention is directed to a method for inducing an immune response, comprising the steps of measuring a subject's mesolimbic activity by fMRI, presenting a representation of the subject's mesolimbic activity to the subject simultaneously with the measuring, instructing the subject to enter into a meditative state, and instructing the subject to increase the represented mesolimbic activity by optimizing their present meditative state.

In one embodiment, neurofeedback is functional near-infrared spectroscopy (fNIRS). In some embodiments, a method utilizing fNIRS measures brain activity through hemodynamic responses associated with neuron behavior.

In one embodiment, neurofeedback is diffusion-weighted magnetic resonance imaging (DWI or DW-MRI). DWI is common and would be apparent to one of ordinary skill in the art, as an MRI modulus which utilizes diffusion of water molecules to generate contrast in MR images. In one embodiment, DWI comprises diffusion tensor imaging (DTI). In one embodiment, DWI comprises vascular perfusion and white matter diffusion MRI.

In one embodiment, neurofeedback is functional MR spectroscopy (fMRS). fMRS generates spectra of resonances, with the area under peaks in the spectrum representing relative concentrations of metabolites. In one embodiment, a method utilizing fMRS provides multiple spectra and study metabolite concentration dynamics during brain function. In some embodiments, fMRS is dynamic MRS. In some embodiments, fMRS is event-related MRS. In some embodiments, fMRS is time-resolved MRS. In some embodiments, fMRS is functional diffusion-weighted spectroscopy (fDWS). In some embodiments, fDWS determines diffusion properties of brain metabolites after activation of the brain.

In one embodiment, neurofeedback is an EEG (electroencephalogram) neurofeedback. As used herein, "EEG neurofeedback" refers to a subject's EEG activity as the physiological system that is used for neurofeedback. In another embodiment, an EEG waveform vary in frequency of 0.01 to 100 Hz. In another embodiment, an EEG is recorded from an electrode sensor placed on or in the brain. In another embodiment, EEG is recorded from an electrode sensor placed on the scalp surface. In another embodiment, in EEG neurofeedback the brain wave profile is presented to the subject and the subject is rewarded for changing the profile. In another embodiment, a reward includes, but not limited to, a pleasant-sounding tone, a continuous tone, a dichotomous tone, a visual display, or others.

In one embodiment, neurofeedback according to the method of the present invention comprises any combination of fMRI, fNIRS, DWI or DW-MRI, fMRS and EEG neurofeedback.

Any neurofeedback modality is applicable as long as it maintains/achieves the activation of neurons of the mesolimbic network.

One of ordinary skill in the art would appreciate applying neurofeedback as described hereinabove as part of medication or improvement thereof.

As used herein, the term "subject" refers to any subject, particularly a mammalian subject, for whom therapy is desired, for example, a human.

In the description and claims of the present application, each of the verbs, "comprise", "include" and "have" and conjugates thereof, are used to indicate that the object or objects of the verb are not necessarily a complete listing of components, elements or parts of the subject or subjects of the verb.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

In the description unless otherwise stated, adjectives such as "substantially" and "about" modifying a condition or relationship characteristic of a feature or features of an embodiment of the invention, are understood to mean that the condition or characteristic is defined to within tolerances that are acceptable for operation of the embodiment for an application for which it is intended. Unless otherwise indicated, the word "or" in the specification and claims is considered to be the inclusive "or" rather than the exclusive or, and indicates at least one of, or any combination of items it conjoins.

In the description and claims of the present application, each of the verbs, "comprise", "include" and "have" and conjugates thereof, are used to indicate that the object or objects of the verb are not necessarily a complete listing of components, elements or parts of the subject or subjects of the verb.

Other terms as used herein are meant to be defined by their well-known meanings in the art.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

EXAMPLES

Materials and Methods fMRI-NF Training Sessions

An intermittent feedback protocol is applied with each NF run consisting of five NF cycles. Each NF practice session will include three NF runs, resulting in fifteen cycles per session (approximately 25 minutes). In EEG-NF practice, multiple sessions are employed. In fMRI-NF, fewer sessions are usually applied (between one and four sessions), probably due to scanning costs, and perhaps since fMRI provides a more accurate measure for specific functions. According to a pilot study of mesolimbic reward network regulation, it was found that the largest mesolimbic reward network modulations were observed during fourth session. Therefore, four NF practice sessions are applied, resulting in sixty NF cycles. Immediately after the fourth session, which is expected to induce the strongest neural modulations, subjects receive Hepatitis B vaccination.

NF Transfer Task

A transfer task at the end of each NF practice session is applied, during which subjects receive similar instruction to those they received during the NF task, only without feedback screen presentation at the end of a regulation phase i.e., subjects apply their mental strategies without feedback guidance. Therefore, BOLD activations in this task point to the applicative potential of our manipulation.

Functional MRI Rest Scans

In order to assess the neural correlates of cytokines concentrations before NF practice, after NF practice and before vaccination, and three days following vaccination (when cytokines concentrations are expected to reach their peak), a functional rest scans are applied during these sessions. During rest scans, subjects are instructed to fix their gaze on a cross, centered on a black screen, and to move as little as possible.

Immunological Data

Blood is collected from all participants at the Ichilov medical center, Tel-Aviv. Blood plasma is separated from serum using centrifugation and then stored in −80° C.; additionally, whole blood samples is stored for later analysis. For effective preservation of the whole blood samples, a Smart Tube proteomic stabilizer buffer (PROT1) is added to the whole blood samples prior storage in −80° C. to ensure proteomic stabilization. Samples are transferred to the Technion, Haifa, to a neuroimmunology lab for immunological analyses.

As part of the characterization of the innate and adaptive immune response to vaccination, Antibodies against HBV in blood plasma (IgM and IgG) is quantified using Chemiluminescent Microparticle ImmunoAssay (CMIA); tumor necrosis factor alpha (TNFα), interferon gamma (IFNγ), interleukin (IL)-6 and IL-4, Cytokines concentrations in blood plasma are quantified using Enzyme-Linked Immuno-Sorbent Assay (ELISA).

Example 1

Neuromodulation Induces an Immune Response

The inventors implemented anew software for fMRI-NF, which enabled them to customize it to the specific needs; then a fMRI-NF session targeting mesolimbic areas (the VTA in the midbrain) of six participants were performed. The results reflect the inventors' analysis of fMRI modulation (NF versus baseline) of the mesolimbic system tested areas. Based on the neurofeedback pilots, the inventors had set several important study parameters, such as task length, means of individually selecting a brain region for regulation, routines of communications with subjects during practice, etc. Importantly, other than utilizing the neurofeedback paradigm, the inventors validated that mesolimbic activity dynamics vary in a substantial way, such that subjects were able to modulate it within a single session, by applying different mental strategies (as was evident in the offline analysis).

Figure 4A:
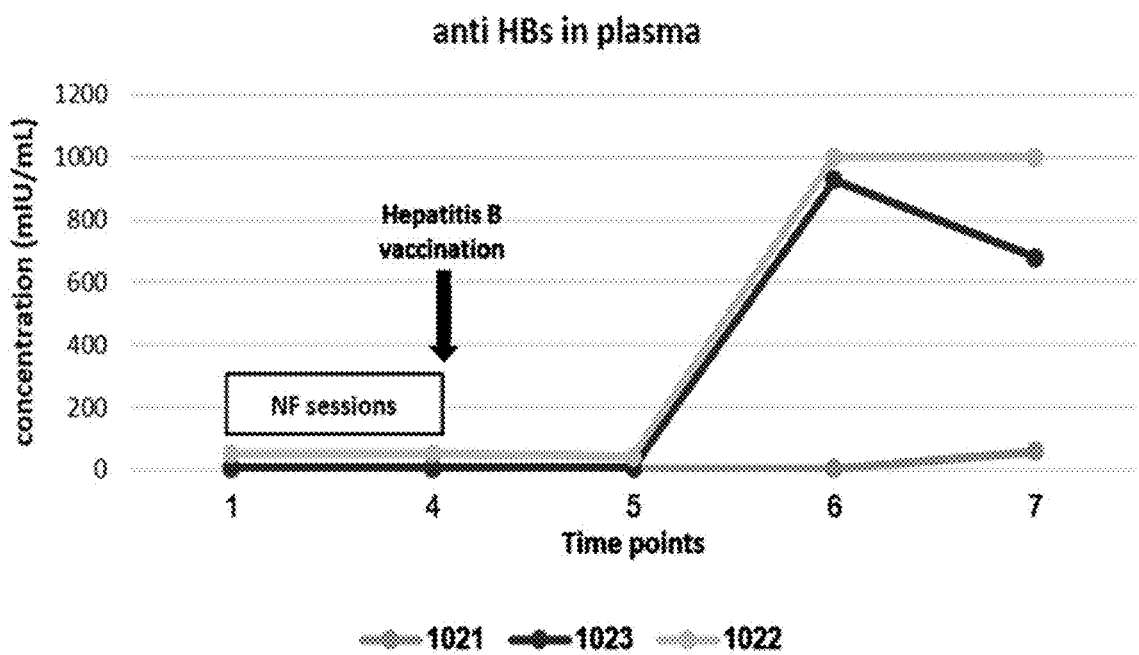
FIGS. 4A-4B are graphs showing immunological analyses of blood samples obtained from the subjects of (FIG. 3). Hepatitis B surface antibodies were determined in the plasma during the different sampling time-points. Following VTA NF sessions, subjects were vaccinated against Hepatitis B surface antigen (HBs). Blood samples were taken for HBs antibody (anti-HBs) measurements (using enzyme-linked immunosorbent assay) at five different time points (TP) (4A): TP1, before NF sessions; TP4, after NF at the day of vaccination; TP5, 5 days post vaccination; TP6, 14 days post-vaccination; TP7, 28 days post-vaccination. (4B) is a graph showing a logarithmic scale fold-change of anti-HBs concentrations in subjects' plasma, before and after vaccination.
Figure 4B:
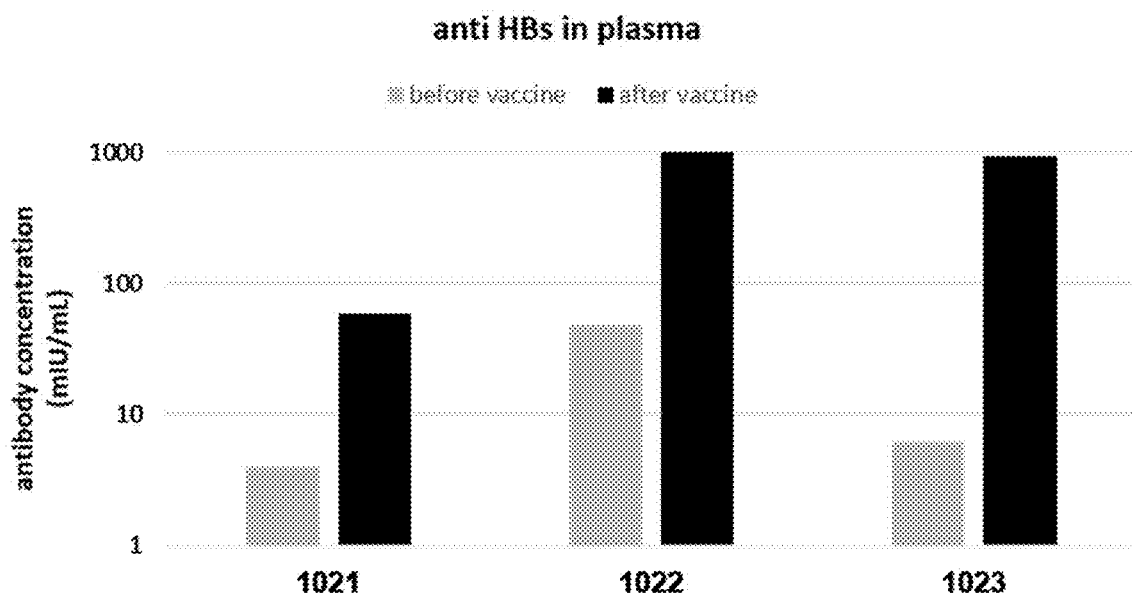

Further to the above, subjects were vaccinated against Hepatitis B surface antigen (HBs) and blood samples were taken for HBs antibody (anti-HBs) measurements. Immunological results were shown to positively correlate with neuromodulation effects (FIG. 4). Therefore, neurofeedback modulation can induce an immune response.

Example 2

Upregulating Mesolimbic Pathway by Co-Activation the VTA and VS

Figure 5A:
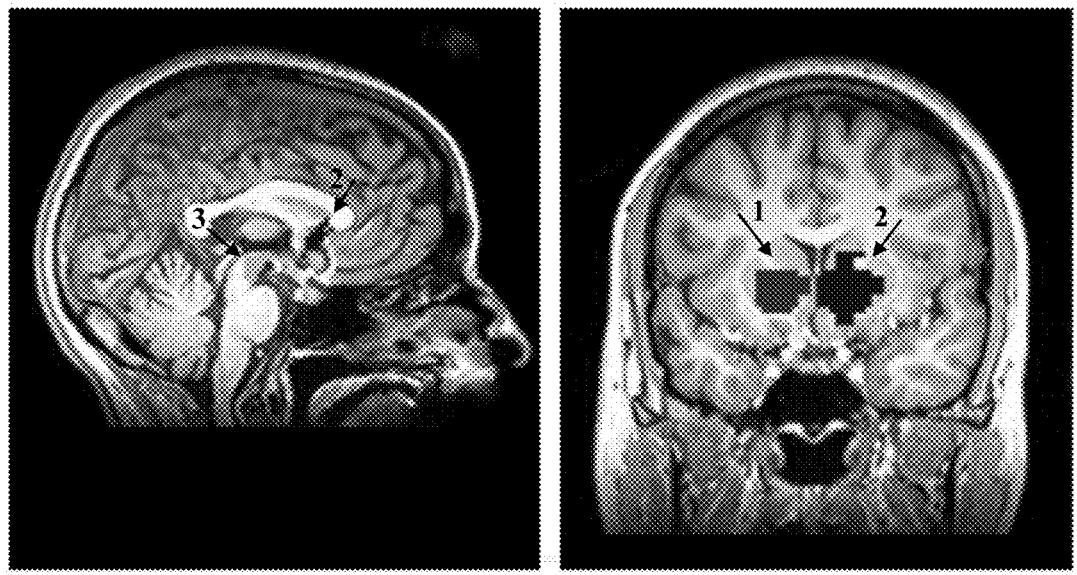
FIGS. 5A-5B are images and graphs of one subject pilot training session. (5A) is images showing selected regions: right ventral striatum (arrow number 1), left ventral striatum (arrow number 2), and VTA (arrow number 3). (5B) are graphs showing the BOLD levels of two NF runs from the pilot training session of (5A). The three regions were found to substantially correlate.
Figure 5B:
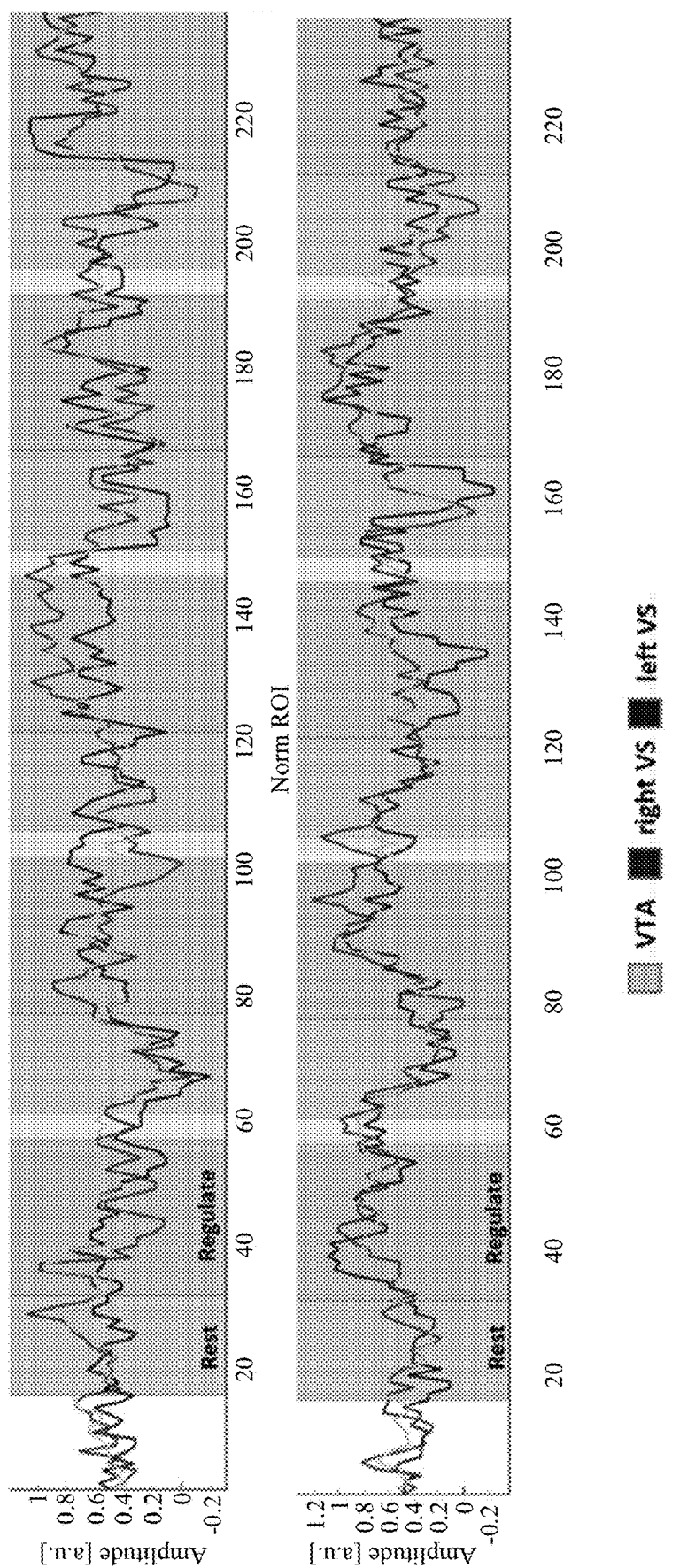

The inventors pursued a more precise and effective mesolimbic modulation paradigm. In this respect, three additional pilot studies were performed which included mesolimbic network NF, up-regulating the co-activation of three main mesolimbic nodes, anatomically defined and restricted based on neurosynth.org meta-analysis results of reward circuitry functional activations. This network is known to comprise the VTA and the bilateral ventral striatum. As was evident from the results, the three regions were substantially correlated (FIG. 5), indicating a functional relationship between them. Therefore, co-activation of both the VTA and VS by means of neurofeedback can upregulate the mesolimbic pathway and subsequently the induced immune response.

Example 3

Mesolimbic Pathway Activation by NF Improves Vaccination Effectiveness

Fifteen (15) participants, are randomized into three groups: mesolimbic network NF group; control-region-of-interest (ROI) NF group, and no treatment group (blood tests and vaccination only). The two active NF study groups are used to assess both the correlational and the causal relationship between mesolimbic volitional modulation and immunological effects. The 'no treatment' group is used to assess the consistency of normal immunological response to Hepatitis B vaccination, and thus constitutes a comparative group for the assessment of immunological effects sizes. Either a correlation between mesolimbic activation and immunological effects, or a consistent and measurable immunological response to Hepatitis B vaccination, is considered a satisfactory result, and therefore indicates improved vaccination effectiveness.

Example 4

Figure 7:
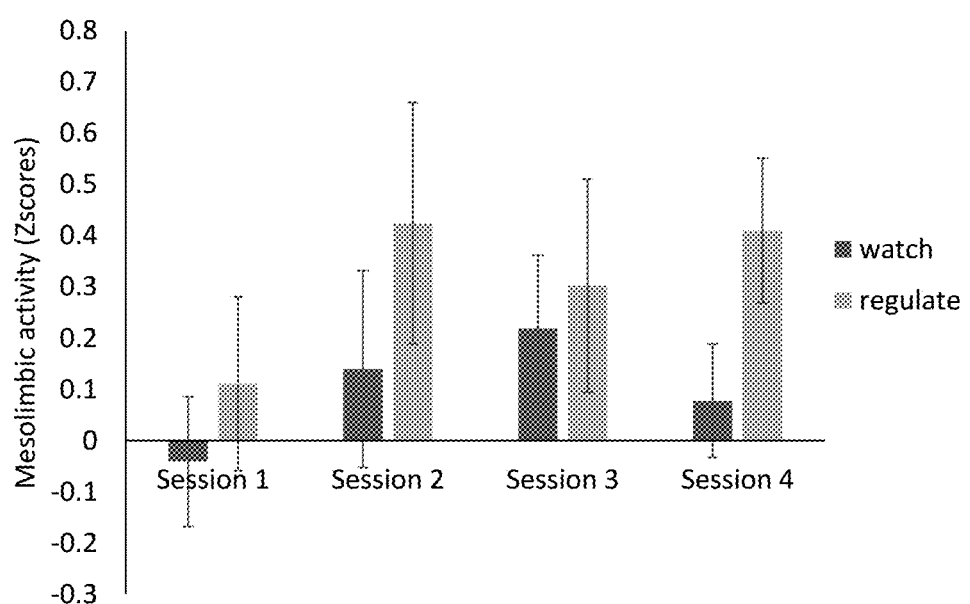
FIG. 7 is a vertical bar graph showing NF success (regulate vs watch) per session. When inspecting the differences between task conditions for each practice session separately, it was revealed that while during the 1st session subjects have not gained the ability to induce mesolimbic activity in a substantial manner, during the next sessions subjects improved in this aspect, while differences between conditions reached their peak at the fourth session. N=10.
Figure 8:
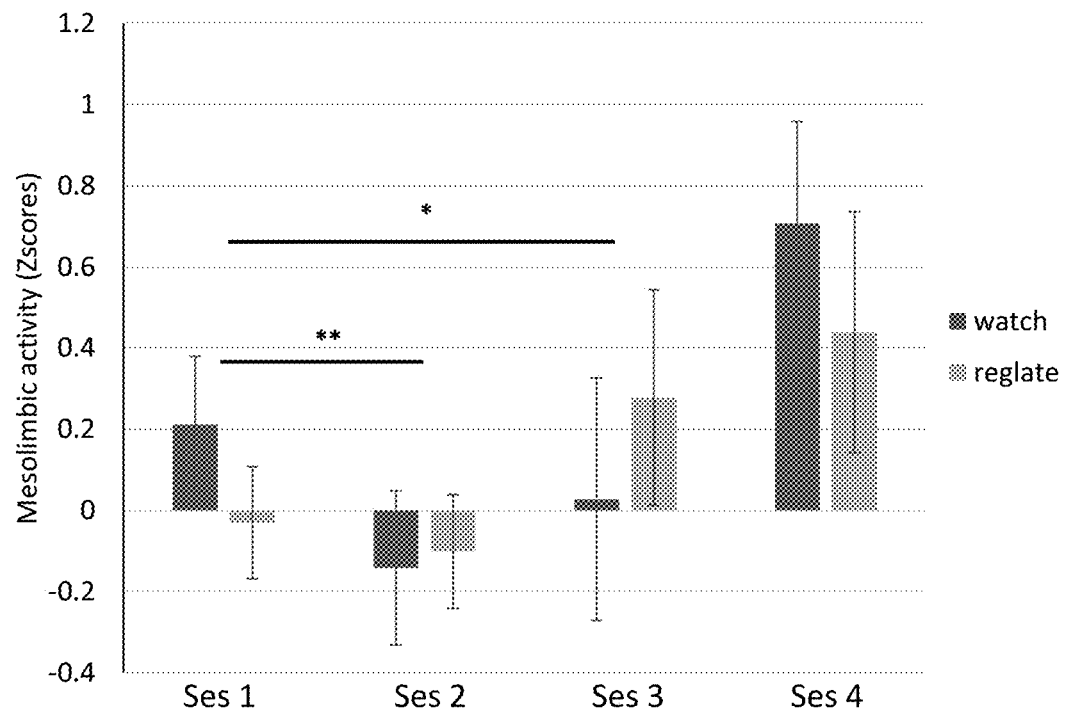
FIG. 8 is a vertical bar graph showing mesolimbic activity during the transfer task (No feedback). Significant differences in ML-network BOLD activations were found between $2^{nd}$ session and $1^{st}$ session (**p=0.018, n=10) and between $3^{rd}$ and $1^{st}$ session (*p=0.026, n=8). Results indicate that subjects gradually learn to up-regulate their ML system even without feedback.

The Ability of Subjects to Self-Modulate Deeply Located Nodes of the Mesolimbic Reward Network Via fMRI-NF Revealing a causal link between the mesolimbic reward network activity and immunological effects demands the substantial and precise induction of the mesolimbic reward network, which might seem challenging. For that aim, the inventors customized a state-of-the-art fMRI-NF software (OpenNFT) for our desired mesolimbic reward network regulation, by using an intermittent feedback protocol, which dissociates feedback reward cues from the regulation phase, thus allowing a cleaner measure of regulation success that is uncontaminated by external reward cues. Furthermore, the inventors speculated that in order to facilitate our desired dopaminergic, reward-related activity, one should up-regulate the mesolimbic reward circuit, i.e., the VTA along with its upstream dopaminergic counterparts—the bilateral ventral striatum, thereby further ensuring the excitation of the desired neural mechanism. Finally, to answer the question of whether subjects can self-induce substantial neural activation in the designated regions via fMRI-NF protocol, the inventors conducted a pilot study. Ten (10) healthy subjects participated in two to four fMRI-NF practice sessions to the mesolimbic reward network. Data were analyzed using the pipeline described above. Results are presented in FIGS. 6-8.

Figure 6:
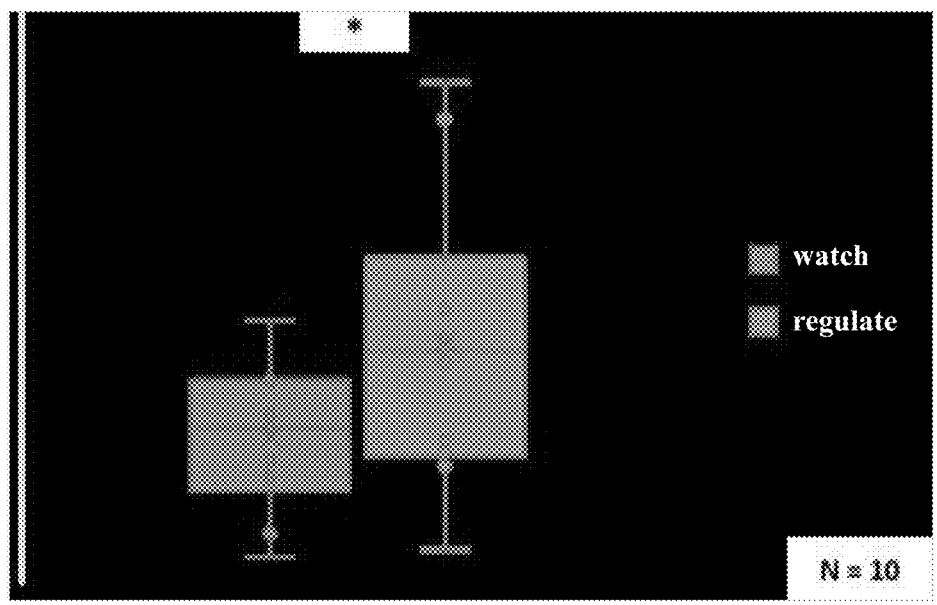
FIG. 6 is a boxplot graph showing mesolimbic (ML) NF training. Average BOLD activations across all NF practice sessions in the ML reward network during "watch" and "regulate" conditions. T test comparisons revealed a significant differences between conditions (*p=0.027, N=10) indicating that subjects were able to upregulate their mesolimbic activity using various mental strategies.

The inventors found a significant difference in BOLD activations between NF task conditions in the desired direction (regulate>watch; FIG. 6), indicating that subjects were able to upregulate their mesolimbic activity. Moreover, from FIG. 7 it is indicated that overall differences were not the result of a general task engagement or confounds of effort, but stem from the gradual development of regulation skills endowed to subjects with practice. Consequently, these results suggest that the customized fMRI-NF protocol facilitates substantial neural activations in the designated mesolimbic reward network, in order for to examine its link to immunological outcome measures.

To examine whether subjects have learned to regulate their mesolimbic activity without feedback, and thus to gather evidence on the applicative potential of the intervention, the inventors applied a transfer task at the end of each NF practice session, during which subjects received similar instruction to those they received during the NF task, only without feedback presentation. Results are presented in FIG. 8.

Example 5

Immunological Outcome Measures Assessment

In order to test the effect of neural regulation on the immune system, the inventors chose HBV as a defined immunological challenge with known dynamics, and as outcome measures the developed antibodies in blood serum and cytokines, assessed 3, 14 and 28 days following vaccination. However, as Hepatitis B vaccination (HBV) is considered quite effective, and as most adults have been vaccinated in their infancy, and some later, two reasonable concerns have been raised, the first is that baseline HB antibodies levels may vary between subjects according to their vaccination history, which may introduce noise to our data and hamper tangible conclusions. Second, the vaccine may induce an immunological response which is too large and unvarying in order to further affect its magnitude via neuromodulation (i.e. a possible ceiling effect). In order to assess these limitations and to acquire preliminary evidence on immunological effects following HBV vaccination, seven subjects have participated in a pilot study. Four subjects completed the full study protocol (FIG. 6), and additional three subjects completed a no-NF study protocol to assess baseline immunological effects. Results are presented in FIGS. 9-10.

Figure 9:
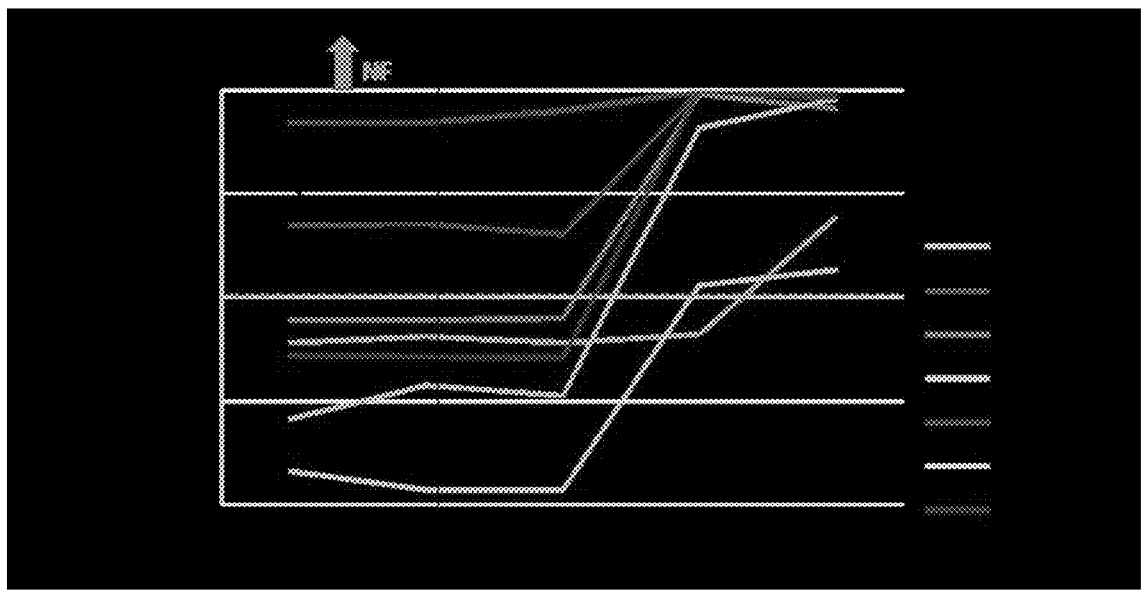
FIG. 9 is graphs showing HBV antibodies in plasma (mIU/mL), before and after ML-NF (green hues) or in no-NF control condition (red hues). Upper panel: pre (mean TP1&TP4 levels) and post (mean TP6&TP7 levels) HBV antibodies concentrations. Note the large difference in baseline among individuals (two subjects were previously vaccinated). The post vaccination measurements seem to differ among individuals. Lower panel: measurements in all 5 time-points; TP1, before NF sessions; TP4, before vaccination; TP5, day 5 post vaccination; TP6, day 14 post vaccination; TP7, day 28 post vaccination.
Figure 10A:
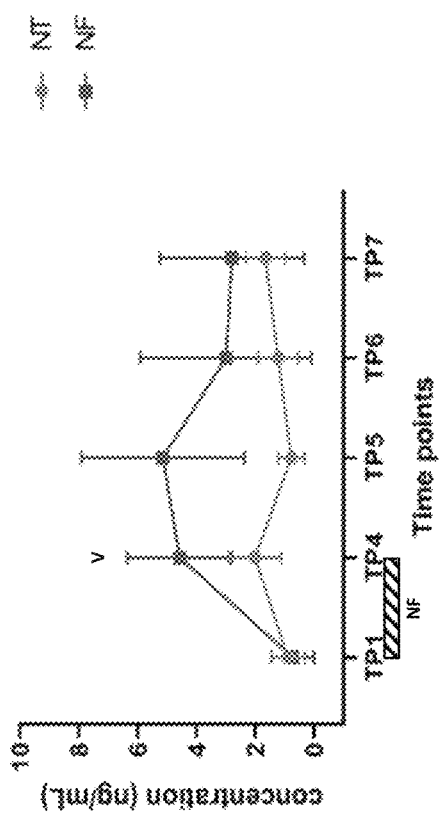
FIGS. 10A-10D are graphs showing the quantification of concentrations of secreted cytokines tumor necrosis factor alpha (TNFα, 10A); interferon gamma (IFNγ, 10B); interleukin (IL)-6 (10C); and IL-4 (10D) in plasma of subjects, at all five blood-sampling time points, presented as mean±SEM for each experimental group. No NF control group (NT) (n=3); or mesolimbic reward modulation (NF; n=3). TP1, before NF sessions; TP4, before vaccination (V); TP5, day 5 post vaccination; TP6, day 14 post vaccination; TP7, day 28 post vaccination.
Figure 10B:
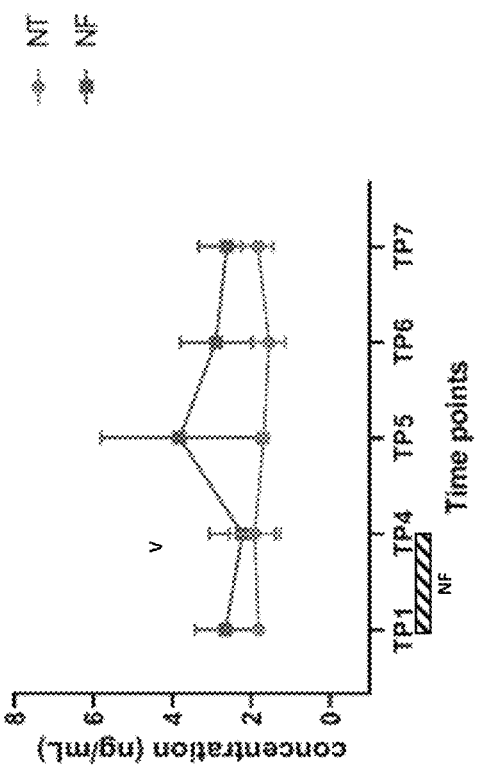
Figure 10C:
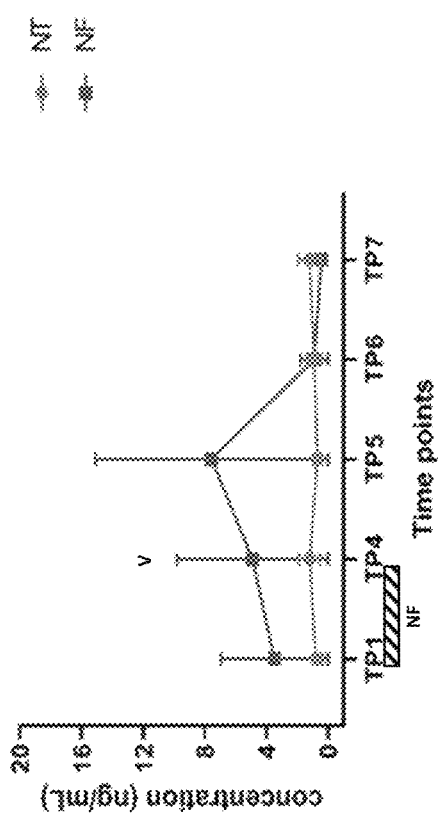
Figure 10D:
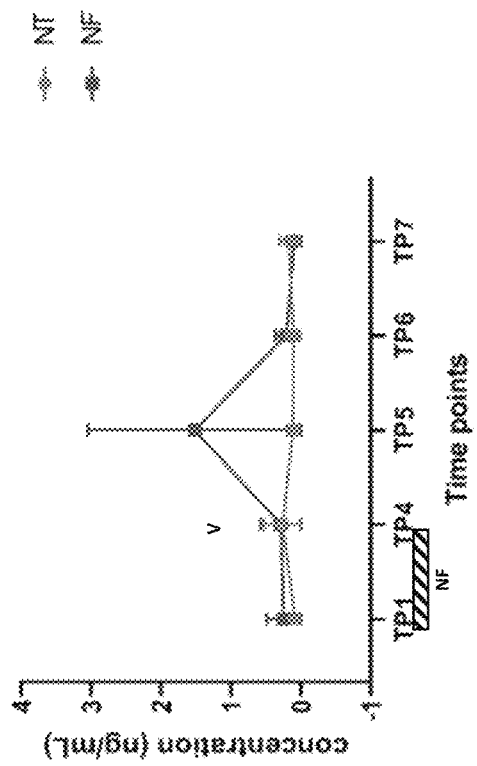

As indicated in FIG. 9, two subjects exhibited high baseline levels of HBV antibodies prior to vaccination. Importantly, these two subjects have reported receiving one out of three (NF_sub-02) or all three (noNF_sub-01) Hep. B shots ~10 years prior to the experiment. Thus, the inventors validated the exclusion criteria regarding vaccination history, thereby minimizing the contamination of the results with variable baseline levels. Furthermore, the post-test immunological responses (both HBV and cytokines) were variable across subjects, both in magnitude and in temporal dynamics. Crucially, this answered the concern of possible ceiling effects: even though post-vaccination antibodies development were strong in general, subjects substantially vary in this outcome measure dynamics. For example, while most individuals showed increased antibody count at 14 days after vaccination, one subject showed increased levels at TP7, 28 days post-vaccination. Similarly, while most individuals reached a plateau after this initial rise, others exhibited further increase or decrease. Together these results indicate the importance of the timing of immunological measurements as capturing the critical period.

The inventors further examined cytokines levels across all time points. FIG. 10 shows a clear pattern of change specifically among individuals that underwent the NF training prior to vaccination.

NF subjects showed increased levels 5 days following vaccination (TP5), indicating stronger immunological response to the vaccination. Even though these results should be interpreted with caution, they nevertheless provide insightful evidence for the possible outcome of the current design.

While certain features of the invention have been described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A method for increasing vaccination efficacy in a subject administered therewith, comprising the step of activating a mesolimbic neuron in said subject by applying a neurofeedback prior to vaccination of said subject, thereby increasing the vaccination efficacy in the vaccinated subject.

2. The method of claim 1, wherein said mesolimbic neuron is located in the ventral tegmental area (VTA), the bilateral ventral striatum (VS), or a combination thereof.

3. The method of claim 1, wherein said activating a mesolimbic neuron comprises co-activating a neuron located in the VTA and a neuron located in the VS.

4. The method of claim 1, wherein said increased vaccination efficacy comprises increased concentration, titer, biological half-life, amount, or any combination thereof, of antibodies in the plasma of the neurofeedback applied subject, compared to control.

5. The method of claim 4, wherein said vaccination efficacy is determined based on an antibody concentration in the plasma, an antibody biological half-life in the plasma, or a combination thereof, compared to control.

6. The method of claim 1, wherein said neurofeedback comprises electroencephalography, functional magnetic resonance imaging, functional near-infrared spectrometry, diffusion-weighted magnetic resonance imaging, functional magnetic resonance spectrometry, or a combination thereof.

7. The method of claim 1, wherein said subject is afflicted with an immunodeficient disease.

8. The method of claim 1, wherein said subject is afflicted with an infectious disease.

9. The method of claim 1, wherein said subject is afflicted with cancer.

10. The method of claim 8, wherein said infectious disease is a viral disease.

11. The method of claim 1, further comprising vaccinating said subject after said applying.

12. A method for treating a subject afflicted with an immunodeficiency the method comprising: (i) activating a mesolimbic neuron in said subject by applying a neurofeedback; and (ii) vaccinating the subject of (i), thereby treating the subject afflicted with the immunodeficiency.

13. A method for increasing vaccination efficacy in a subject in need thereof, the method comprising: (i) selecting a subject having previously been applied with neurofeedback to a mesolimbic neuron; and (ii) vaccinating the subject of (i), thereby increasing the vaccination efficacy in the subject.

* * * * *